(12) United States Patent
Birdwell et al.

(10) Patent No.: US 7,266,174 B2
(45) Date of Patent: Sep. 4, 2007

(54) RADIOGRAPHIC INSPECTION OF AIRFRAMES AND OTHER LARGE OBJECTS

(75) Inventors: Thomas William Birdwell, Middletown, OH (US); Thomas Edward Bantel, Cincinnati, OH (US)

(73) Assignee: General Electric Company, Schenectady, NY (US)

( * ) Notice: Subject to any disclaimer, the term of this patent is extended or adjusted under 35 U.S.C. 154(b) by 0 days.

(21) Appl. No.: 11/073,504

(22) Filed: Mar. 7, 2005

(65) Prior Publication Data

US 2006/0198498 A1    Sep. 7, 2006

(51) Int. Cl.
    *G01B 15/06* (2006.01)
(52) U.S. Cl. .......................................... 378/58; 378/114
(58) Field of Classification Search ........ 378/204–205, 378/57–58, 95, 114
    See application file for complete search history.

(56) References Cited

U.S. PATENT DOCUMENTS

| | | | | |
|---|---|---|---|---|
| 3,952,201 | A * | 4/1976 | Hounsfield | ...................... 378/8 |
| 5,463,668 | A | 10/1995 | Kagaya | |
| 5,541,856 | A | 7/1996 | Hammermeister | |
| 6,229,872 | B1 * | 5/2001 | Amos | .......................... 378/58 |
| 6,461,040 | B1 * | 10/2002 | Mattson et al. | ............. 378/205 |
| 6,466,643 | B1 | 10/2002 | Bueno et al. | |
| 6,507,635 | B2 | 1/2003 | Birdwell et al. | |
| 6,542,570 | B1 * | 4/2003 | Silver | ............................. 378/4 |
| 6,577,889 | B2 * | 6/2003 | Ichihashi | ..................... 600/425 |
| 6,614,872 | B2 | 9/2003 | Bueno et al. | |
| 6,618,465 | B2 | 9/2003 | Mohr et al. | |
| 6,633,775 | B1 * | 10/2003 | Bernard | ...................... 600/428 |
| 6,662,088 | B1 * | 12/2003 | Hopple et al. | ................ 701/29 |
| 2002/0181653 | A1 | 12/2002 | Birdwell et al. | |
| 2003/0147493 | A1 | 8/2003 | Bueno et al. | |
| 2003/0152189 | A1 * | 8/2003 | Li et al. | ......................... 378/8 |
| 2003/0188757 | A1 * | 10/2003 | Yanof et al. | ................ 128/916 |
| 2004/0010210 | A1 * | 1/2004 | Avinash et al. | ............. 600/595 |
| 2004/0039420 | A1 * | 2/2004 | Jayne et al. | .................... 607/5 |
| 2004/0070753 | A1 * | 4/2004 | Sugihara et al. | ......... 356/237.5 |

FOREIGN PATENT DOCUMENTS

| | | |
|---|---|---|
| EP | 1376104 A1 | 1/2004 |
| FR | 2237606 A | 2/1975 |
| JP | 2004061289 * | 2/2004 |

\* cited by examiner

*Primary Examiner*—Edward J. Glick
*Assistant Examiner*—John M Corbett
(74) *Attorney, Agent, or Firm*—Adams Evans P.A.; William Scott Andes

(57) ABSTRACT

A system for radiographic inspection of an object includes a radiation source located on one side of the object and a radiation detector located on another side of the object, being positioned to receive radiation from the radiation source. At least one motion sensor is associated with the radiation detector, the radiation source, or the object, for detecting motion. The magnitude of motion of the components is compared to a pre-established limit value. The imaging process is conducted when the magnitude of any motion is less than the limit value.

19 Claims, 4 Drawing Sheets

RADIOGRAPHIC INSPECTION OF AIRFRAMES AND OTHER LARGE OBJECTS

BACKGROUND OF THE INVENTION

This invention relates generally to radiographic inspection and more particularly to a method of radiographic inspection of large objects such as airframes.

Aircraft, including their fuselages and nacelles, and other large structures, often require periodic inspection to verify their structural condition. This may be done visually or with non-destructive evaluation (NDE) techniques. Because of the complicated physical structure of aircraft fuselages and nacelles, radiographic inspection, such as X-ray inspection, is used to avoid the disassembly of overlapping components, insulation, wall coverings, etc. Modern digital electronic detectors are replacing X-ray film in many X-ray inspection applications. It is often difficult to position these detectors in contact with the inspected structure. Thus the detector and the structure are often not in physical contact and do not always move together. This results in blurred images and reduced ability to discern defects. This condition is further exacerbated with electronic detectors as geometric magnification and/or extended exposure times are sometimes used to improve image resolution. Both of these techniques increase sensitivity to any relative motion between the structure and the detector.

Unwanted motion is especially of concern in the inspection of very large objects such as airframes and aircraft engine nacelles. The physical size and arrangement of these objects results in the X-ray source and detector being mounted on different supports and thus having separate motion. Because of the large size of these objects, the X-ray source and detector mounting structures must be large enough to provide range of motion necessary to cover the entire object. For example, to inspect an aircraft fuselage, one might use a ground based cantilevered boom-like device to position the X-ray source or detector over the top of the fuselage. This would require a very large boom, over 30 feet in the case of a large aircraft. This extended reach device may have significant motion at the end of the boom, including vibration and harmonic motion from the residual inertia after movement of the device. Further, the large objects themselves often move during imaging. This may be due to wind, personnel working on the aircraft, and the like.

Accordingly, there is a need for a method to ensure the motion of the components during a radiographic imaging period is not large enough to negatively impact the quality of the image.

BRIEF SUMMARY OF THE INVENTION

The above-mentioned need is met by the present invention, which according to one aspect provides a system for radiographic inspection of an object, including: a radiation source located on one side of the object; a radiation detector located on another side of the object, the radiation detector being positioned to receive radiation from the radiation source; and at least one motion sensor associated with each of the radiation detector and the object for detecting motion thereof. Means are provided for comparing a magnitude of the motion to a pre-established limit value.

According to another aspect of the invention, a method of radiographic inspection of an object includes: providing a radiation source located on one side of the object; providing a radiation detector located on another side of the object; positioning the radiation detector to receive radiation from the radiation source; detecting the magnitude of motion of at least the radiation detector and the object; establishing a limit value for the magnitude of the motion; and comparing the magnitude of the motion to the limit value. An imaging process of the object is initiated when the magnitude is less than the limit value.

According to another aspect of the invention a system for radiographic inspection of an aircraft includes: a radiation source carried by a first manipulator operable to position the radiation source on one side of an area of interest of the aircraft; a radiation detector carried by a second manipulator operable to position the radiation detector on another side of the area of interest of the aircraft such that the radiation detector can receive radiation from the radiation source; at least one first sensor associated with the aircraft for detecting motion thereof; at least one second sensor associated with the radiation detector for detecting motion thereof; and means for comparing a magnitude of motion of each of the aircraft and the radiation detector to pre-established limit values thereof.

BRIEF DESCRIPTION OF THE DRAWINGS

The invention may be best understood by reference to the following description taken in conjunction with the accompanying drawing figures in which.

DETAILED DESCRIPTION OF THE INVENTION

Figure 1:
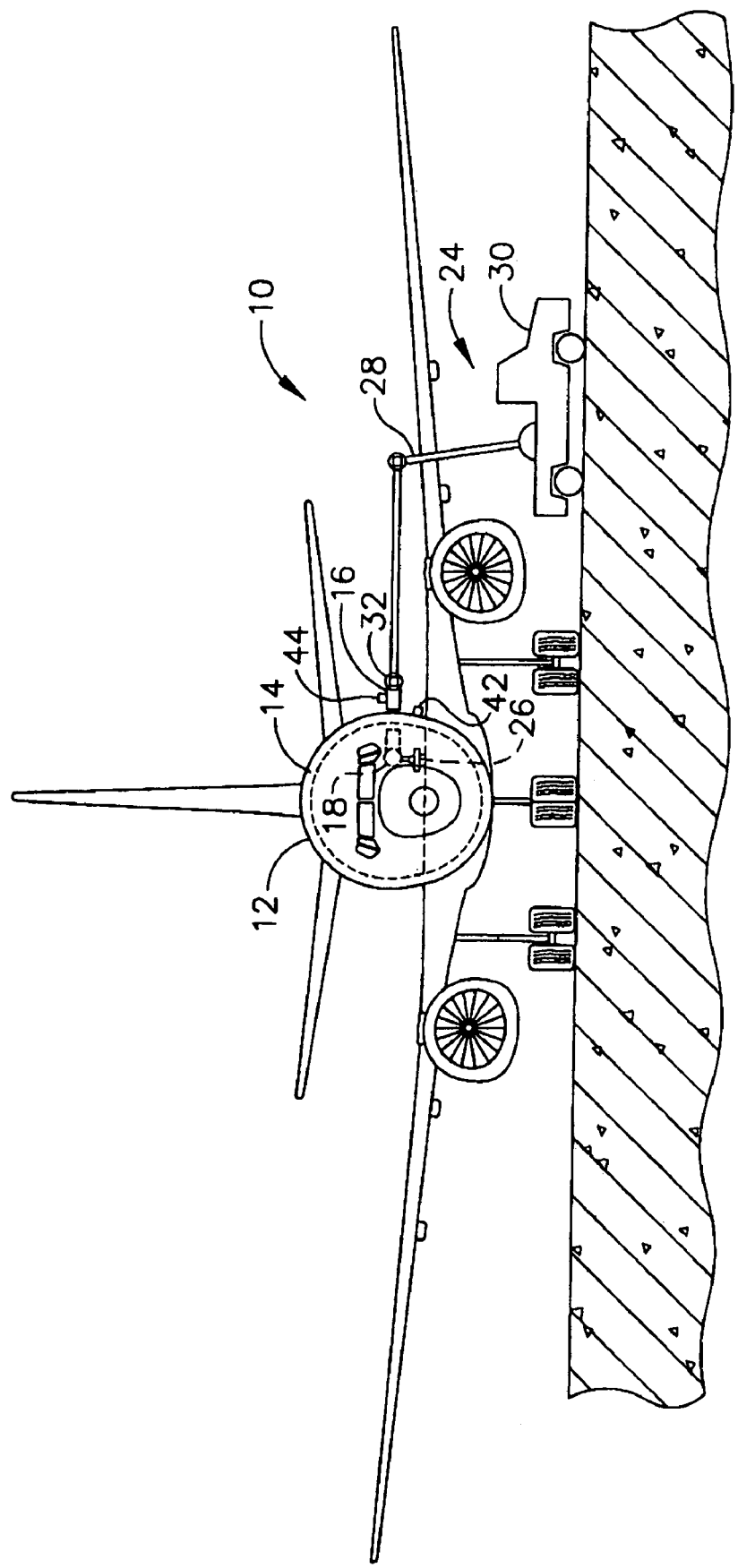
FIG. 1 is a schematic front view of an inspection system constructed according to one aspect of the present invention and positioned around an aircraft.

Referring to the drawings wherein identical reference numerals denote the same elements throughout the various views, FIG. 1 illustrates schematically a radiographic inspection system 10 for inspecting an aircraft fuselage 12. The fuselage 12 generally comprises a cylindrical wall 14 made up of a grid of circumferential frame members and longitudinal stringers covered by a skin of lightweight sheet metal. The inspection system 10 may be used with other types of structures as well. The inspection system 10 includes a radiation source 16 located on a first side of the fuselage wall 14 and a radiation detector 18 located on a second, opposite side of the fuselage wall 14. The radiation source 16 and radiation detectors 18 are relatively situated on opposite sides of the wall 14 so that radiation emitted by the radiation source 16 irradiates the fuselage wall 14 and then impinges on the radiation detector 18. As depicted in FIG. 1, the radiation source 16 is located outside of the fuselage 12, and the radiation detector 18 is located inside of the fuselage 12. However, it should be noted that this arrangement could alternatively be reversed so that the radiation source 16 is inside and the radiation detector 18 is outside the fuselage 12.

The radiation source 16 may be a standard industrial x-ray tube powered by a high voltage power supply (not shown). Alternative radiation sources, such as an isotopic radiation source producing gamma rays, could be used as well. The radiation source 16 provides a large cone-shaped or panoramic volume radiation flux, but is collimated to limit this to a specific area of interest. The radiation detector 18 can be any means that is capable of processing radiation emitted by the radiation source 16 into a viewable image. Although X-ray film could be used, it is generally, but not necessarily, preferred that the radiation detector 18 be of the type that converts impinging radiation into an electrical output signal. Many suitable X-ray detectors are commercially available. As is known in the art, such X-ray detectors generally have an X-ray sensitive area and means for producing an output signal that is indicative of the X-rays impinging on the sensitive area.

Figure 2:
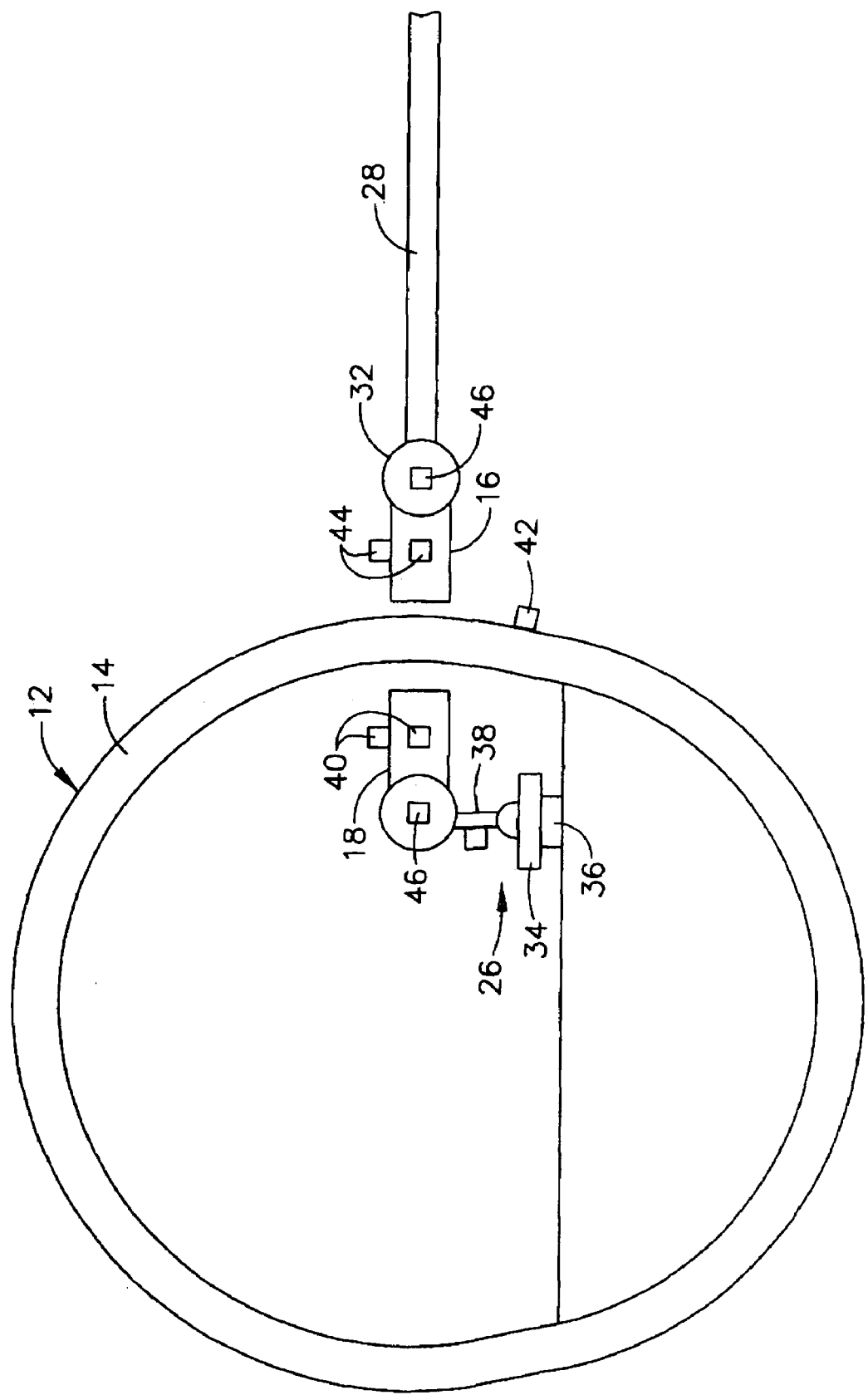
FIG. 2 is a schematic cross-sectional view of an aircraft fuselage with a radiation detector and source positioned for inspection thereof.

A first manipulator 24 is provided for moving the radiation source 16 with respect to the fuselage 12, and a second manipulator 26 is provided for moving the radiation detector 18 with respect to the fuselage 12. The manipulators 24, 26 can be any type of device capable of producing the desired motion. This would include robotic devices, guide rail systems and the like. As shown in FIGS. 1 and 2, the first manipulator 24 comprises an articulated boom 28 mounted to a carrier vehicle 30. The boom 28 may be of a known type in which gross multiple-axis movement of the various members is provided by hydraulic actuators (not shown). The radiation source 16 may be attached to the boom 28 by a precise manipulator 32 which enables small, controlled motions of the radiation source 16. In the illustrated example, the second manipulator 26 comprises a base 34 mounted on a rail 36 which extends parallel to the longitudinal axis of the fuselage 12. The radiation detector 18 is attached to the base 34 with a manipulator arm 38. The base 34 can be driven forward and aft along the rail 36 by an electric motor (not shown), and the manipulator arm 38 is able to move the radiation detector 18 in one or more axes to position it as required.

Figure 4:
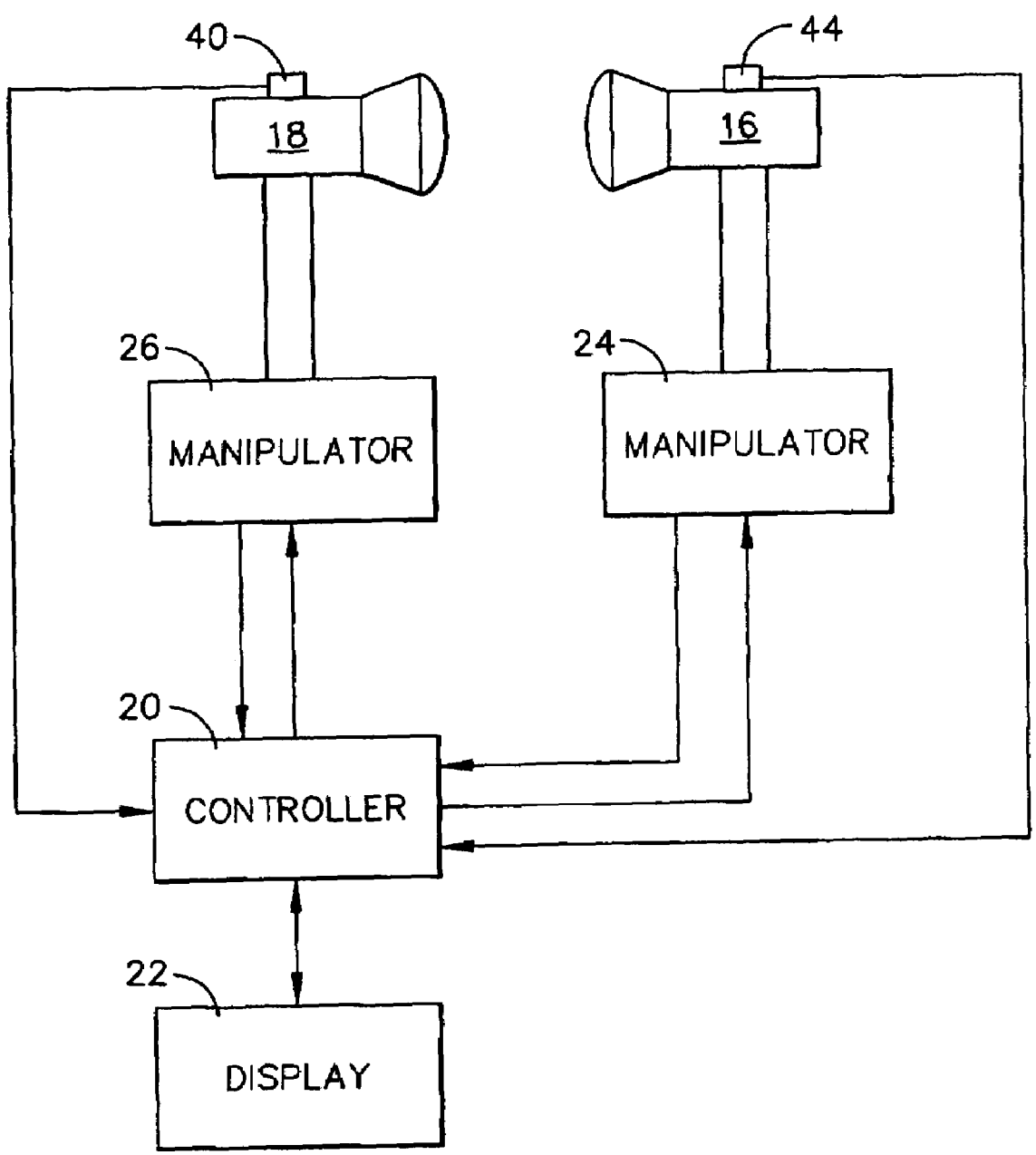
FIG. 4 is a schematic view of a radiation source and detector operatively connected to a controller.

Referring now to FIG. 4, the image data signals output by the radiation detector 18 are fed to a controller 20, which can be a conventional computer unit. The controller 20 processes these signals and causes corresponding images to be displayed on a display 22. An operator is then able to view the displayed images to inspect for defects in the fuselage 12. The data image signals are also stored in a memory in the controller 20. The controller 20 also controls the operation of the radiation source 16, turning it on and off and regulating the voltage applied.

Figure 3:
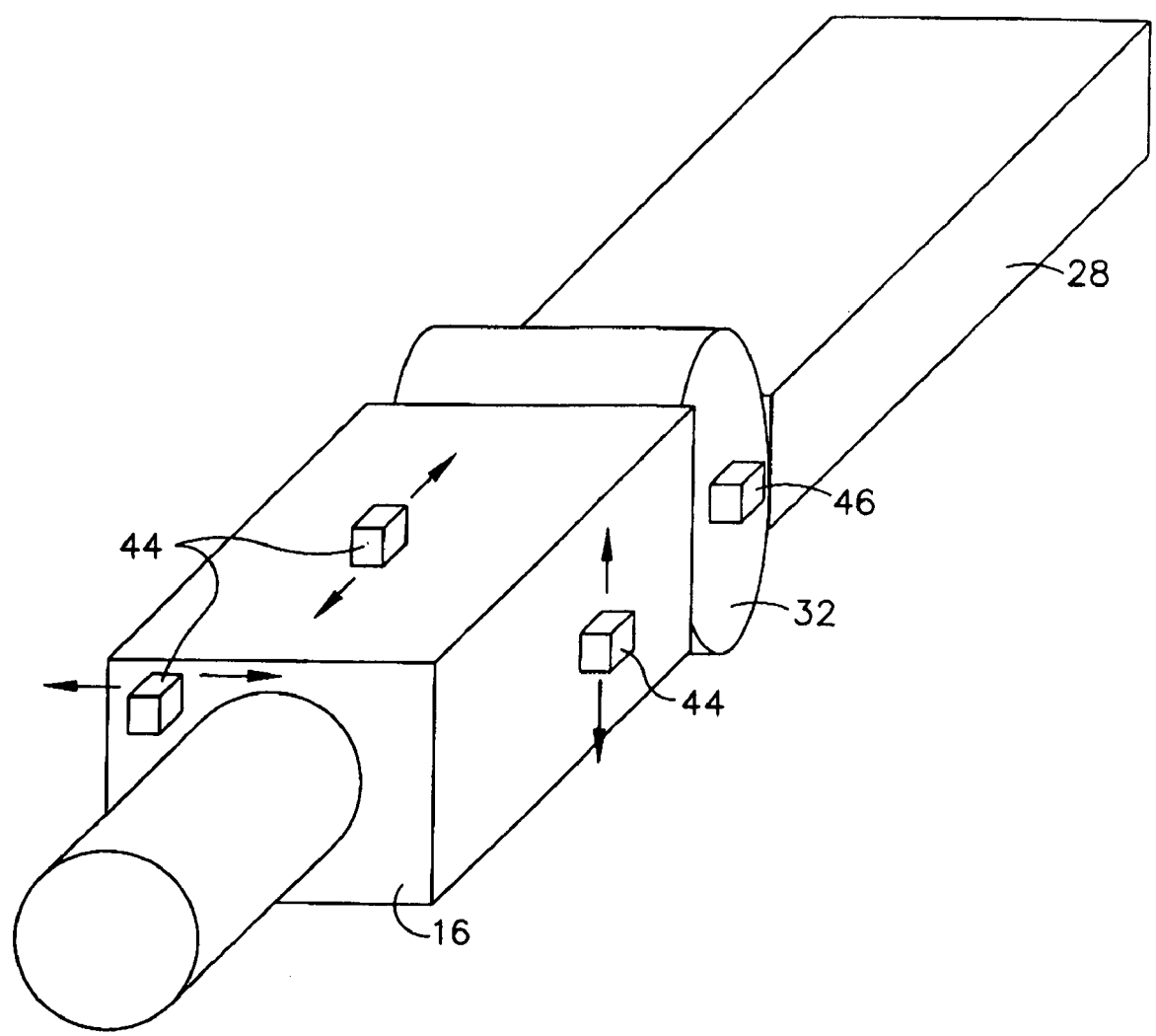
FIG. 3 is a schematic perspective view of a radiation source having a motion sensor attached thereto.

The inspection system includes at least one motion sensor. For example, as shown in FIGS. 2 and 3, accelerometers 40, 42, and 44 of a known type may be mounted on the radiation detector 18, the fuselage 12, and the radiation source 16 respectively. One accelerometer may be used for each axis of motion, as indicated by the arrows in FIG. 3. The accelerometers 40, 42, 44 directly measure the acceleration of the associated component. Other aspects of motion, such as velocity and displacement, may be measured if a suitable type of integrating accelerometer is used. Other types of motion sensors may be used as well. For example, motion of the radiation detector 18 or the radiation source 16 may be measured by detecting the deflection of the moveable joints of the first and second manipulators 24 and 26 with deflection-type motion sensors 46 attached thereto, such as rotary encoders, linear transducers, or the like.

In operation, the first and second manipulators 24 and 26 are controlled to move the radiation source 16 into alignment with an area of interest on the fuselage 12 and with the radiation detector 18 so that the detector 18 will be exposed to radiation from the radiation source 16, under the direction of the controller 20. Because of the relatively large size of the fuselage 12, the radiation source 16, first manipulator 24, radiation detector 18, and second manipulator 26, there may be significant motion at the end of the boom 28, including vibration and harmonic motion from the residual inertia after movement of the radiation source. Further, the fuselage 12 may move during imaging. This may be caused by wind, personnel working on the aircraft, and the like. Therefore, after the radiation detector and source 18 and 16 are positioned, the output of the motion sensors 40, 42, 44 or 46 is analyzed to determine if the magnitude of motion of the components during the image period is large enough to negatively impact the quality of the image.

As used herein, the term "magnitude" is intended to encompass any aspect of the motion which can be correlated to image quality. This could be the displacement, the velocity, or the acceleration. Limit values are pre-established for the magnitude of motion of each component based on the known characteristics of the radiation detector 18 and the radiation source 16. If the magnitude of motion exceeds one or more of the limit values, the imaging process is delayed until the motion abates below the respective limit value. This analysis may be manual or automated. For example, the output of the motion sensors may be presented on the display 22 so that an operator can determine whether or not to begin the imaging process. Alternatively, the controller 20 (or a software program running on the controller 20) may receive input signals from the motion sensors, compare the signals to the pre-established limit values, and either inhibit the imaging process until the magnitude of the motion is below the limit values, or automatically initiate the imaging process when magnitude of the motion falls below the limit values Once the magnitude of the motion is within acceptable limits, the radiation source 16 is then turned on so that the adjoining region of the fuselage 12 is illuminated with radiation. Radiation emitted by the radiation source 16 passes through the fuselage wall 14 and impinges on the radiation detector 18. The radiation is converted into electrical signals that are fed to the controller 20. The controller 20 processes these signals and causes corresponding images to be displayed on a display 22. An operator is then able to view the displayed images to inspect for defects in the fuselage 12. The data image signals are also stored in a memory in the controller 20. The data may also be fed to a computer (not shown) for computer-based image evaluation, or for pre-processing before viewing by the operator. While the imaging is taking place, the motion of the fuselage 12, the radiation detector 18, and the radiation source 16 may be continuously monitored If the limit values for the motions are exceeded, the operator or the controller 20 may terminate the imaging process, wait for the motion to abate, and then re-start the imaging process. Image quality indicators, such as a line pair gage can be included in the image view. After the imaging process is complete, the controller 20 or operator can determine if the image sharpness is sufficient and then repeat the imaging process. Known features of the fuselage 12, for example rivets or other fasteners, can be evaluated in a manner similar to the line pair gage, to achieve the same goal.

The foregoing has described a method and apparatus for radiographic inspection of large objects. While specific embodiments of the present invention have been described, it will be apparent to those skilled in the art that various modifications thereto can be made without departing from the spirit and scope of the invention. Accordingly, the foregoing description of the preferred embodiment of the invention and the best mode for practicing the invention are provided for the purpose of illustration only and not for the purpose of limitation, the invention being defined by the claims.

What is claimed is:

1. A system for improving the quality of radiographic inspection of an aircraft, comprising:
   (a) a radiation source for being positioned on one side of the aircraft;

(b) a radiation detector for being positioned in relation to the aircraft and the radiation source to receive radiation transmitted through the aircraft from the radiation source;

(c) at least one motion sensor associated with the radiation detector and the aircraft for detecting motion of the aircraft prior to radiation transmission;

(d) comparison means for comparing a magnitude of the motion to one or more pre-established limit values thereof to determine whether the motion is sufficiently low to result in a satisfactory image, and outputting a result indicative of the comparison; and (e) initiation means for initiating radiographic inspection of the aircraft when the result indicates motion is sufficiently low to result in a satisfactory image.

2. The system of claim 1 wherein the motion sensor is an accelerometer.

3. The system of claim 1 wherein the motion sensor is an integrating accelerometer.

4. The system of claim 1, and further including a display for presenting an output signal from the motion sensor representative of the magnitude of the motion.

5. The system of claim 1, and further including a controller operable to compare the magnitude of the motion to the one or more pre-established limit values and to inhibit an imaging process when the magnitude of the motion is at or above the one or more pre-established limit values.

6. The system of claim 1 further comprising a controller operable to compare the magnitude of the motion to the one or more pre-established limit values during an imaging process and to terminate the imaging process when the magnitude of the motion is at or above the one or more pre-established limit values.

7. A method for improving the quality of radiographic inspection of an aircraft, comprising the steps of:

(a) positioning a radiation source on one side of the aircraft;

(b) positioning a radiation detector in relation to the aircraft and the radiation source to receive radiation transmitted through the aircraft from the radiation source;

(c) detecting motion of the aircraft prior to radiation transmission; (d) comparing a magnitude of the motion to a pre-established limit value thereof to determine whether the motion is sufficiently low to result in a satisfactory image;

(e) outputting a result indicative of the comparison; and (f) initiating radiographic inspection of the aircraft when the result indicates motion is sufficiently low to result in a satisfactory image.

8. The method of claim 7, and further comprising the steps of:

(a) monitoring a motion of at least one of the radiation source and the radiation detector during an imaging process; and (b) terminating the inspection when the motion of at least one of the radiation source and the radiation detector exceeds a limit value during the imaging process.

9. The method of claim 8, and further comprising the steps of:

(a) detecting the magnitude of motion of the radiation source;

(b) establishing a limit value for the magnitude of the motion of the radiation source; and (c) comparing the magnitude of the motion of the radiation source to the limit value for the magnitude of motion of the radiation source, and initiating the imaging process of the aircraft when the magnitude of the motion of the radiation source is less than the limit value for the magnitude of motion of the radiation source.

10. The method of claim 8, wherein the magnitude of the motion is an acceleration.

11. The method of claim 8, wherein the magnitude of the motion is a velocity.

12. The method of claim 8, wherein the magnitude of the motion is a displacement.

13. The method of claim 9, wherein the steps of comparing the magnitude of the motion of the radiation source to the limit value for the magnitude of the motion of the radiation source and initiating the imaging process are performed by a controller operably connected to the radiation source and the radiation detector.

14. A system for radiographic inspection of an aircraft, comprising:

(a) a radiation source carried by a first manipulator operable to position the radiation source on one side of an area of interest of the aircraft;

(b) a radiation detector carried by a second manipulator operable to position the radiation detector on another side of the area of interest of the aircraft such that the radiation detector can receive radiation transmitted through the area of interest from the radiation source;

(c) a first sensor associated with the aircraft for detecting motion of the aircraft prior to radiation transmission;

(d) a second sensor associated with the radiation detector for detecting motion thereof prior to radiation transmission;

(e) comparison means for comparing magnitudes of motion of the aircraft and the radiation detector to pre-established limit values thereof to determine whether the motions are sufficiently low to result in a satisfactory image and outputting a result indicative of the comparison; and (f) initiation means for initiating radiographic inspection of the aircraft when the result indicates motion is sufficiently low to result in a satisfactory image.

15. The system of claim 14, wherein each of the first and second sensors comprise at least one accelerometer attached to the aircraft and the radiation detector, respectively.

16. The system of claim 14, and further comprising:

(a) a third sensor associated with the radiation source for detecting motion thereof; and (b) comparison means for comparing a magnitude of motion of the radiation source to a preestablished limit value thereof.

17. The system of claim 16, wherein the third sensor comprises at least one accelerometer attached to the radiation source.

18. The system of claim 14, wherein the second sensor comprises a sensor which detects deflection mounted to the second manipulator.

19. The system of claim 14, further including a display for presenting an output signal from the first or second sensor representative of the magnitude of the respective motion.

* * * * *